United States Patent [19]

Sartorelli et al.

[11] Patent Number: 6,040,338

[45] Date of Patent: Mar. 21, 2000

[54] N,N-BIS(SULFONYL)HYDRAZINES USEFUL AS ANTINEOPLASTIC AGENTS

[75] Inventors: Alan C. Sartorelli, Woodbridge; Krishnamurthy Shyam, Hamden; Philip G. Penketh, Hamden; Shu-Hui Chen, Hamden, all of Conn.

[73] Assignee: Yale University, New Haven, Conn.

[21] Appl. No.: 08/963,182

[22] Filed: Nov. 3, 1997

[51] Int. Cl.[7] .................................................. A61K 31/27
[52] U.S. Cl. ........................... 514/482; 514/117; 560/13; 560/142; 560/145; 560/148
[58] Field of Search .................................. 514/117, 482; 560/13, 148, 142, 145

[56] References Cited

U.S. PATENT DOCUMENTS

| | | | |
|---|---|---|---|
| 4,684,747 | 8/1987 | Sartorelli et al. | 564/81 |
| 4,806,531 | 2/1989 | Sartorelli et al. | 514/183 |
| 4,892,887 | 1/1990 | Sartorelli et al. | 514/601 |
| 4,939,072 | 7/1990 | Morigaki et al. | 430/372 |
| 4,962,114 | 10/1990 | Sartorelli et al. | 514/311 |
| 5,101,072 | 3/1992 | Sartorelli et al. | 564/81 |
| 5,214,068 | 5/1993 | Sartorelli et al. | 514/601 |
| 5,256,820 | 10/1993 | Sartorelli et al. | 564/81 |
| 5,281,715 | 1/1994 | Sartorelli et al. | 546/306 |
| 5,637,619 | 6/1997 | Sartorelli et al. | 514/590 |

OTHER PUBLICATIONS

Thornber, C.W., 'Isosteriesm and Molecular Modification in Drug Design,' Chemical Society Reviews, vol. 18, No. 4, pp. 563–580, 1979.

K. Shyam et al., Antitumor 2–(Aminocarbonyl)–1, 2–bis(methylsulfonyl)–1–(2–chloroethyl)–hydrazines, Journal of Medical Chemistry, 1996, vol. 39, No. 3, pp. 796–801.

K. Shyam et al., 1,2–Bis(sulfonyl)hydrazines. 3. Effects of Structural Modification on Antineoplastic Activity, Journal of Medical Chemistry, 1987, vol. 30, No. 11, pp. 2157–2161.

K. Shyam et al., Synetheis and Evaluation of 1–Acyl–1, 2–bis(methylsulfonyl)–2–)2–chloroethyl)hydrazines as Antineoplastic Agents, Journal of Medical Chemistry, 1993, vol. 36, No. 23, pp. 3496–3502.

K. Shyam et al., Synthesis and Evaluation of 1,2,2–Tris(sulfonyl)hydrzines as Antineoplastic and Typanocidal Agents, Journal of Medical Chemistry, 1990, vol. 33, No. 8, pp. 2260–2264.

B. Teicher et al., Nitrobenzyl Halides And Carbamates As Prototype Bioreductive Alkylating Agents, Journal of Medical Chemistry, vol. 23, 1980, pp. 955–960.

K.A. Kennedy et al., The Hypoxic Tumor Cell: A Target For Selective Cancer Chemotherapy, Biochem. Pharmacol, vol. 29, 1980, pp. 1–8.

A.J. Lin et al., Potential Bioreductive Alkylating Agent, In: Cancer Chemotherapy, Sartorelli, A.C. (ed.), American Chemical Society, 1976, pp. 71–86.

Moore, H.W. et al., Naturally Occurring Quionones As Potential Bioreductive Alkylating Agents, Med. Res. Rev., vol. 1, 1981, pp. 249–280.

Brown, J.M. et al., Therapeutic Advantage Of Hypoxic Cells In Tumors: A Theoretical Study, J. Nat'l. Cancer Inst., vol. 83, 1991, pp. 178–185.

Jenkins, T.C., Hypoxia–selective Agents: Radiosensitizers And Cytotoxins, In: The Chemistry of Antitumor Agents, Wilman, (ed.), 1990, pp. 342–369.

Wilson, W.R. et al.,Selective Toxicity Of Nitracine To Hypoxic Mammalian Cells, Br. J. Cancer, vol. 49, 1984, pp. 215–223.

Zeman, E.M. et al., SR–4233: A New Bioreductive Agent With High Selective Toxicity For Hypoxic Cells, Int. J. Radiat. Oncol. Biol. Phys., vol. 12, 1986, pp. 1239–1242.

Kirkpatrick, D.L. et al., Nitrobenzyl Derivatives As Bioreductive Alkylating Agents: Evidence For the Reductive Formation Of A Reactive Intermediate, Journal of Medical Chemistry, vol. 29, 1986, pp. 2048–2052.

Tercel, M. et al., Nitrobenzyl Mustard Quaternary Salts: A New Class of Hypoxia–Selective Cytotoxins Showing Very High In Vitro Selectivity, Journal of Medical Chemistry, vol. 36, 1983, pp. 2578–2579.

Tercel, M. et al., Hypoxia–Selective Antitumor Agents. 12. Nitrobenzyl Quaternary Salts As Bioreductive Prodrugs Of The Alkylating Agent Mechlorethamine, Journal of Medical Chemistry, vol. 39, 1996, pp. 1084–1094.

Mulcahy, R.T. et al., Nitrobenzyl Phosphorodiamidates As Potential Hypoxia–selective Alkylating Agents, Journal of Medical Chemistry, vol. 37, 1994, pp. 1610–1615.

Denny, W.A. et al., Bioreducible Mustards: A Paradigm For Hypoxia–selective Progrugs Of Diffusible Cytotoxins (HPCDs), Cancer Met. Rev., vol. 12, 1993, pp. 135–151.

(List continued on next page.)

*Primary Examiner*—Peter O'Sullivan
*Attorney, Agent, or Firm*—Todd E. Garabedian; Wiggin & Dana

[57] ABSTRACT

The present invention relates to a compound of the formula

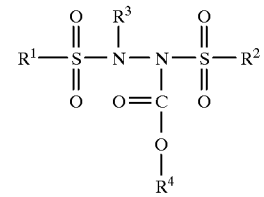

wherein $R^1$ and $R^2$ are selected from lower alkyl groups having 1–6 carbon atoms, substituted or unsubstituted aryl groups, and unsaturated alkyl groups having 1–6 carbon atoms; $R^3$ is a substituted or unsubstituted lower alkyl group having 1–6 carbons; and $R^4$ is selected from substituted or unsubstituted lower alkyl groups having 1–6 carbon atoms, substituted or unsubstituted aryl groups, and unsaturated alkyl groups having 1–6 carbon atoms. The present invention also relates to a pharmaceutical composition comprising the above compound, as well as a method of treating tumor cells with the compound.

11 Claims, 4 Drawing Sheets

OTHER PUBLICATIONS

Moulder, J.E. et al., Hypoxic Fractions Of Solid Tumors: Experimental Techniques, Methods Of Analysis, And A Survey Of Existing Data, Int. J. Radiat. Oncol. Biol. Phys., vol. 10, 1984, pp. 695–712.

Sartorelli, A.C., Therapeutic Attack Of Hypoxic Cells Of Solid Tumors: Presidential Address, Cancer REs., vol. 48, 1988, pp. 775–778.

Stewart, D.J. et al., Non–chemotherapeutic Agents That Potentiate Chemotherapy Efficacy, Cancer Treat. Rev, vol. 16, 1989, p. 1940.

N,N-BIS(SULFONYL)HYDRAZINES USEFUL AS ANTINEOPLASTIC AGENTS

STATEMENT OF GOVERNMENT SUPPORT

This invention was made in part with government support under grant number CA-53340 from the National Cancer Institute. The government has certain rights in this invention.

BACKGROUND OF THE INVENTION

1. Field of the Invention

The invention relates to N,N'-bis(sulfonyl)hydrazines, and more particularly to alkoxy- and aryloxycarbonyl derivatives of N,N'-bis(sulfonyl)hydrazines that have antineoplastic activity.

2. Brief Description of the Art

Solid tumors have been difficult to treat by chemotherapeutic and radiotherapeutic approaches. Inefficient vascularization of the solid tumor during its development results in hypoxic (i.e., oxygen deficient) areas within the tumor mass (Moulder, J. L. and Rockwell, S., Cancer Met. Rev. 5: 313–341, 1987; Sartorelli, A. C., Cancer Res. 48: 775–778 (1988)). This inefficient vascularization gives rise to unique problems in the treatment of tumors. For example, inefficient vascularization of solid tumors results in cells that are starved of oxygen and nutrients, and are either noncycling or slowly progressing through the cell cycle. Thus, these cells are relatively resistant to cell cycle-specific chemotherapy and are more difficult to supply with adequate drug concentrations. The oxygen deficiency of these cells further renders them resistant to oxygen-activated agents such as bleomycin and streptonigrin which require the formation of $O_2$-derived species in order to be efficacious, and to ionizing radiation whose toxicity is oxygen-concentration dependent. Thus, inefficient vascularization of solid tumors and the resulting subpopulation of hypoxic cells limits the choice of useful and effective chemotherapy treatments.

The resistance of tumor cells to a large number of cancer chemotherapeutic agents has also been correlated with increased intracellular levels of glutathione (GSH) and/or glutathione S-transferase (GST) activity (Stewart, D. J. and Evans, W. K., Cancer Treat. Rev. 16: 1–40 (1989)). Many neoplastic cell lines which have not been subjected to drug selection pressures also have intrinsically high levels of GSH, and relatively high levels of GST activity have been found in a variety of human tumors. It is thought that the protective effects are due to spontaneous and enzyme-catalyzed interactions between the sulfhydryl group of the glutathione molecule and the chemotherapeutic agent. Accordingly, in addition to hypoxia, the resistance of various cell lines and human tumors to a variety of chemotherapeutic agents has been attributed to their high non-protein thiol and GST contents.

Radiotherapy treatments have also been largely unsuccessful in the treatment of solid tumors. Hypoxic cells in particular have proven to be resistant to ionizing radiation since the sensitivity to ionizing radiation is dependent upon the concentration of oxygen.

Solid tumors have been treated with chemotherapy and radiotherapy for many years with limited degrees of success. New potential drugs have been developed to address the problem of chemotherapeutic and radiotherapeutic resistance. For example, several classes of nitro-containing synthetic hypoxia-selective agents have been developed, including analogs of nitroimidazoles (Jenkins, T. C., The Chemistry of Antitumor Agents, Wilman, ed., pp. 342–369, Blackie, Glasgow (1990)), nitroacridines (Wilson, W. R., Denny, W. A., Twigden, S. J., Baguely, B. C. and Probert, J. C., Brit. J. Cancer 49: 215–223 (1984)), benzotriazine N-oxides (Zeman, E. M., Brown, J. M., Lemmon, M. J., Hirst, V. K. and Lee, W. W., Int. J. Radiat. Oncol. Biol. Phys. 12: 1239–1242 (1986)), nitrobenzyl halides and carbamates (Teicher, B. A. and Sartorelli, A. C., J. Med. Chem. 23: 955–960 (1980); Kirkpatrick, D. L., Johnson, K. E. and Sartorelli, A. C., J. Med. Chem. 29: 2048–2052 (1986)), nitrobenzyl mustard quaternary salts (Tercel, M., Wilson, W. R. and Denny, W. A., J. Med. Chem. 36: 2578–2579 (1993); Tercel, M., Wilson, W. R., Anderson, R. F. and Denny, W. A., J. Med. Chem. 39: 1084–1094 (1996)), and nitrobenzyl phosphorodiamidates (Mulcahy, R. T., Gipp, J. J., Schmidt, J. P., Joswig, C. and Borch, R. F., J. Med. Chem. 37: 1610–1615 (1994)). All of these classes of compounds are hypothesized to undergo preferential reductive activation in hypoxic cells to generate potent cytotoxins.

1,2-Bis(sulfonyl)-1-methyl- and 1-(2-chloroethyl) hydrazine compounds shown in formula 1 have been identified that possess antineoplastic activity (Shyam, K., Hrubiec, R. T., Furubayashi, R., Cosby, L. A. and Sartorelli, A. C., J. Med. Chem. 30: 2157–2161 (1987); Shyam, K., Penketh, P. G., Divo, A. A., Loomis, R. H., Patton, C. L. and Sartorelli, A. C., J. Med. Chem. 33: 2259–2264 (1990)).

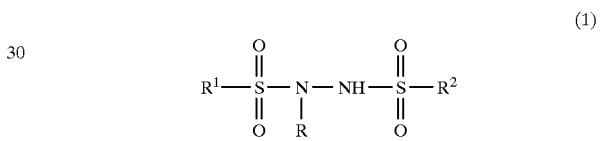

(1)

In formula 1, $R^1$ and $R^2$ are alkyl groups or aryl groups, and R is —$CH_3$ or —$CH_2CH_2Cl$. These compounds are thought to undergo spontaneous decomposition in aqueous media to generate the putative alkylating species $RN=NSO_2R^2$. The most active compound of this class is 1,2-bis(methylsulfonyl)-1-(2-chloroethyl)hydrazine (compound 2) and is described in U.S. Pat. No. 4,892,887 to Sartorelli et al.:

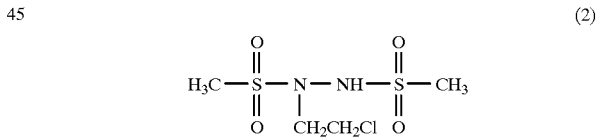

(2)

Compound 2 has been demonstrated to produce 40% cures of mice bearing the L1210 leukemia when administered as a single intraperitoneal dose (Shyam, K., Penketh, P. G., Divo, A. A., Loomis, R. H., Patton, C. L. and Sartorelli, A. C., J. Med. Chem. 33: 2259–2264 (1990)). However, compound 2 is active only over a narrow dosage range. In addition, compound 2 has a relatively short half-life (30 to 40 seconds at pH 7.4 and 37° C.) and exhibits considerable host toxicity. These disadvantages limit the use of compound 2 as an anticancer agent.

Prodrugs of compound 2 have been synthesized as compounds 3 and 4 (Shyam, K., Penketh, P. G., Loomis, R. H., Rose, W. C. and Sartorelli, A. C., J. Med. Chem. 39: 796–801 (1996); Shyam, K., Penketh, P. G., Divo, A. A., Loomis, R. H., Rose, W. C. and Sartorelli, A. C., J. Med.

Chem. 36: 3496–3502 (1993)) and are disclosed in U.S. Pat. Nos. 5,256,820 and 5,637,619:

(3)

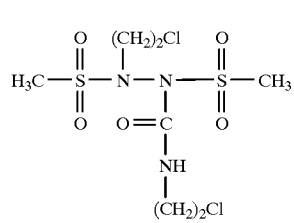

(4)

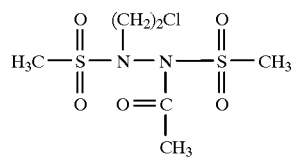

Both compounds 3 and 4 have broad-spectrum antitumor activity and are considerably less toxic to host animals than compound 2. However, compound 3 undergoes spontaneous decomposition in aqueous media similar to that found with compound 2. Compound 4 is more resistant to spontaneous decomposition in aqueous media, but is prone to nonspecific thiol, protease, and plasma catalyzed activation, a major disadvantage to the therapeutic usefulness of this compound.

Additional N,N'-bis(sulfonyl)hydrazines and related chemotherapeutic compounds are disclosed in U.S. Pat. Nos. 5,281,715; 5,214,068; 5,101,072; 4,962,114; 4,849,563; and 4,684,747.

What is needed in the art is a class of chemotherapeutic agents that efficiently and effectively treats neoplastic cells having resistance to conventional chemotherapeutic agents, is relatively stable, and which minimizes host toxicity. The present invention offers a solution to these needs.

SUMMARY OF THE INVENTION

In one aspect, the present invention relates to a compound of the formula

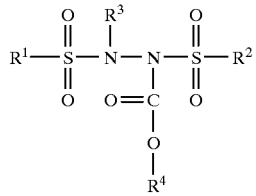

wherein $R^1$ is selected from the group consisting of lower alkyl groups having 1–6 carbon atoms, substituted or unsubstituted aryl groups, and unsaturated alkyl groups having 1–6 carbon atoms; $R^2$ is selected from the group consisting of lower alkyl groups having 1–6 carbon atoms, substituted or unsubstituted aryl groups, and unsaturated alkyl groups having 1–6 carbon atoms; $R^3$ is a substituted or unsubstituted lower alkyl group having 1–6 carbons; and $R^4$ is selected from the group consisting of substituted or unsubstituted lower alkyl groups having 1–6 carbon atoms, substituted or unsubstituted aryl groups, and unsaturated alkyl groups having 1–6 carbon atoms.

In another aspect, the present invention relates to a pharmaceutical composition for treating tumor cells, comprising an antineoplastic agent in a pharmaceutically acceptable carrier, the antineoplastic agent having the formula

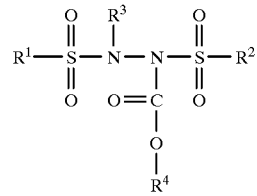

wherein $R^1$ is selected from the group consisting of lower alkyl groups having 1–6 carbon atoms, substituted or unsubstituted aryl groups, and unsaturated alkyl groups having 1–6 carbon atoms; $R^2$ is selected from the group consisting of lower alkyl groups having 1–6 carbon atoms, substituted or unsubstituted aryl groups, and unsaturated alkyl groups having 1–6 carbon atoms; $R^3$ is a substituted or unsubstituted lower alkyl group having 1–6 carbons; and $R^4$ is selected from a substituted or unsubstituted lower alkyl group having 1–6 carbon atoms, a substituted or unsubstituted aryl group, and an unsaturated alkyl group.

In yet another aspect, the present invention relates to a method of inhibiting the growth of L1210 leukemia or EMT6 mammary carcinoma in host organisms, comprising the step of administering to the host organism a growth-inhibiting effective amount of an antineoplastic agent in a carrier, the antineoplastic agent having the formula

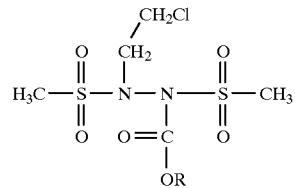

wherein R is selected from methyl, 2-chloroethyl, vinyl, phenyl, p-tolyl, p-chlorophenyl, p-methoxyphenyl, p-nitrobenzyl, benzyl, 4,5-dimethoxy-2-nitrobenzyl, 1-(4-nitrophenyl)ethyl, and a substituent of the formula

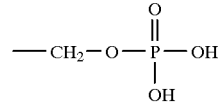

or a pharmaceutically acceptable salt thereof.

These and other aspects will become apparent upon reading the following detailed description of the invention.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1:
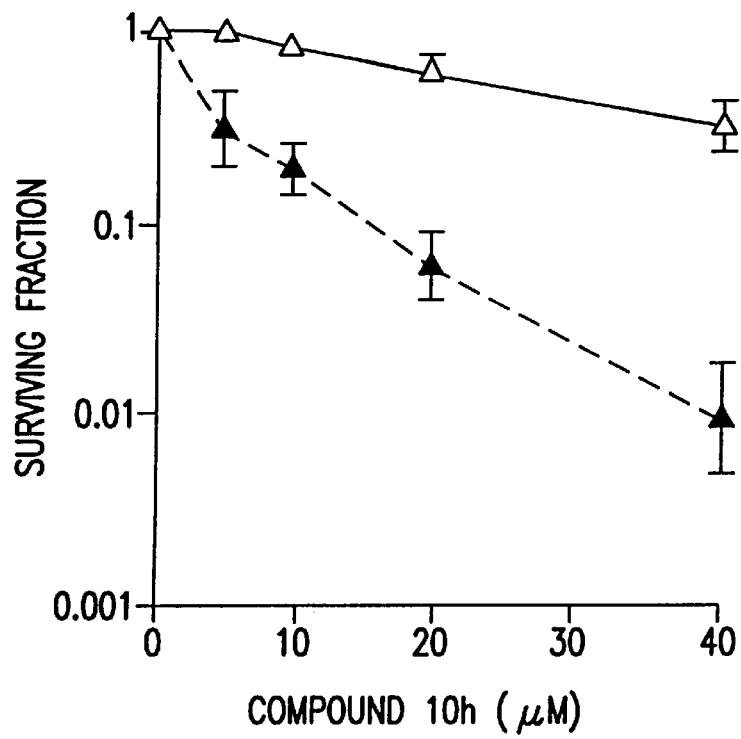
FIG. 1 is a graph of the survival of EMT6 cells exposed to various concentrations of compound 10h for 1 hr under hypoxic or aerobic conditions in vitro.

In accordance with the present invention, a solution is provided to the problem of efficiently and effectively treating neoplastic cells having resistance to conventional chemotherapeutic agents. More specifically, elevated thiol and/or GST levels or areas of hypoxia in solid tumors provide sites of vulnerability which can be preferentially targeted using the agents of the present invention. Using the compounds of the present invention, active antineoplastic agents can be generated from parent molecules that are effective against neoplastic cells having high levels of non-protein thiols or GSH/GST, or are hypoxic.

Toxicity to tumor cells displaying these characteristics has been found to be significantly enhanced by including an alkoxy-or aryloxycarbonyl group (—COOR) in N,N'-bis(sulfonyl)hydrazines to give a carbamate ester:

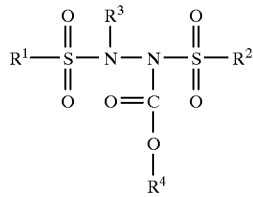

Preferably, $R^1$ and $R^2$ are each independently lower alkyl groups having 1–6 carbon atoms, a substituted or unsubstituted aryl group, or an unsaturated alkyl group. $R^1$ and $R^2$ are most preferably methyl groups.

$R^3$ is a substituted or unsubstituted lower alkyl group having 1–6 carbon atoms. Preferably, $R^3$ is a methyl group (—CH₃) or a 2-haloethyl group (—CH₂—CH₂—X) where X is a halogen atom (e.g., 2-chloroethyl).

$R^4$ is preferably a substituted or unsubstituted lower alkyl group having 1–6 carbon atoms, a substituted or unsubstituted aryl group, or an unsaturated alkyl group. Examples of substituents for $R^4$ include methyl, ethyl, propyl, butyl, haloalkyl (e.g., 2-chloroethyl, 2-bromoethyl), vinyl, phenyl, p-tolyl, halophenyl (e.g., p-chlorophenyl), alkoxyphenyl (e.g., p-methoxyphenyl, p-ethoxyphenyl), nitrophenyl, benzyl, nitrobenzyl, 4,5-dimethoxy-2-nitrobenzyl, halonitrobenzyl (e.g., 4-halo-2-nitrobenzyl, 5-halo-2-nitrobenzyl), 3-methoxy-4-nitrobenzyl, 5-methyl-2-nitrobenzyl, 1-(4-nitrophenyl)ethyl, a substituent of the formula

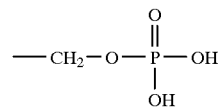

or a pharmaceutically acceptable salt thereof, or a substituent of the formula

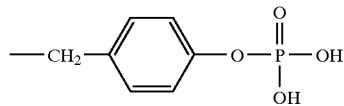

or a pharmaceutically acceptable salt thereof. The most preferred substituents for $R^4$ are p-nitrobenzyl, 4,5-dimethoxy-2-nitrobenzyl, and 1-(4-nitrophenyl)ethyl.

It has been found that a carbamate linkage confers useful advantages to N,N'-bis(sulfonyl)hydrazines. The alkoxy- and aryloxycarbonyl-derived N,N'-bis(sulfonyl)hydrazines are susceptible to thiolysis, as depicted in Scheme I below.

(Scheme 1)

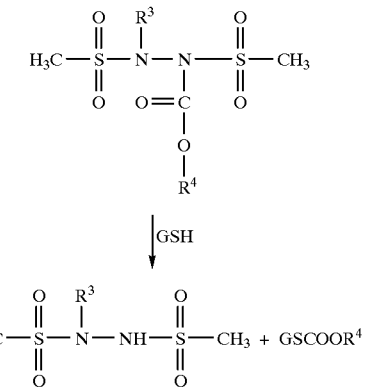

When $R^3$ is a methyl group, the rate of activation by GSH/GST is highly dependent upon the nature of the 2-alkoxy- or 2-aryloxycarbonyl moiety at the $R^4$ position. Table 1 shows relative rates of activation of 1 mM 2-alkoxycarbonyl-1,2-bis(methylsulfonyl)-1-methylhydrazines of the formula $CH_3SO_2N(CH_3)N(COOR^4)SO_2CH_3$ in vitro in the presence of GSH (1 mM) and GST (400 µg/ml). As shown in Table 1, the more electron-withdrawing the $R^4$ group, the greater the relative rate of activation by GSH/GST.

TABLE 1

| Compound | $R^4$ | Relative Activation Rate by GSH/GST |
|---|---|---|
| 6 | —CH₃ | 100 |
| 7 | —C₂H₅ | 30 |
| 8 | —CH₂CH₂Br | 300 |
| 9 | —C₆H₄-4-OCH₃ | 1,700 |

The rate of activation of 2-(2-bromoethoxy)carbonyl-1,2-bis(methylsulfonyl)-1-methylhydrazine (compound 8) was elevated approximately 18-fold in vitro by the presence of GSH (1 mM) and GST (400 μg/ml), compared to buffer alone.

Generally, the N,N'-bis(sulfonyl)hydrazines of the present invention are also more stable in aqueous media than equivalent compounds containing acyl linkages. For example, the initial rates of hydrolysis of 2-acetyl-1,2-bis (methylsulfonyl)-1-methylhydrazine (an acyl derivative shown in structural formula 5) and 1,2-bis(methylsulfonyl)-2-methoxycarbonyl-1-methylhydrazine (a carbamate compound shown in structural formula 6) were 0.3% and 0.007% per minute, respectively, at pH 7.4 and 37° C.

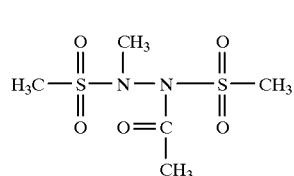
(5)

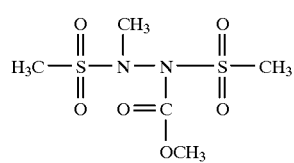
(6)

Furthermore, the rate of decomposition of compound 6 was not appreciably increased by levels of proteinase K or serum that enhanced the rate of activation of compound 5 almost 10-fold.

Based on these data, 2-alkoxycarbonyl-1,2-bis (methylsulfonyl)-1-alkylhydrazines are stable in aqueous media at near-neutral pH values and in serum and can preferentially target tumor cells with elevated GSH and/or GST levels. Thus, these compounds have significant advantages over their acyl counterparts, which are more readily activated by other mechanisms.

In general, chloroethylating agents are more cytotoxic than methylating agents and are preferred for cancer chemotherapy. Accordingly, the preferred compounds of the invention are 2-alkoxycarbonyl- and 2-aryloxycarbonyl-1,2-bis(alkylsulfonyl)- 1-(2-chloroethyl)hydrazines. Particularly preferred 2-alkoxycarbonyl- and 2-aryloxycarbonyl-1, 2-bis(alkylsulfonyl)-1-(2-chloroethyl)hydrazines include the following compounds based on compound 10:

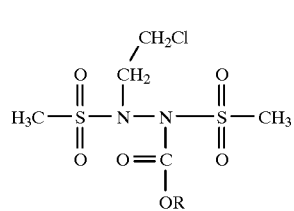
(10)

where R is a substituted or unsubstituted alkyl group, a substituted or unsubstituted aryl group, or an unsaturated alkyl group. Preferred substituents for R are selected from methyl, ethyl, propyl, butyl, haloalkyl (e.g., 2-chloroethyl, 2-bromoethyl), vinyl, phenyl, p-tolyl, halophenyl (e.g., o-, m-, or p-chlorophenyl), alkoxyphenyl (e.g., o-, m-, or p-methoxyphenyl, o-, m-, or p-ethoxyphenyl), nitrophenyl, benzyl, nitrobenzyl (e.g., 2-nitrobenzyl and 4-nitrobenzyl), 4,5-dimethoxy-2-nitrobenzyl, halonitrobenzyl (e.g., 4-halo-2-nitrobenzyl, 5-halo-2-nitrobenzyl), 3-methoxy-4-nitrobenzyl, 5-methyl-2-nitrobenzyl, 1-(4-nitrophenyl)ethyl, a substituent of the formula

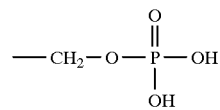

or a pharmaceutically acceptable salt thereof, or a substituent of the formula

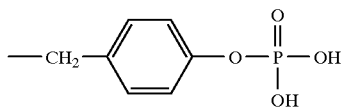

or a pharmaceutically acceptable salt thereof, and the like. Preferred pharmaceutically acceptable salts of the latter two compounds include amine salts such as triethanolamine salt, triethylamine salt, lutidine salt, or other pharmaceutically acceptable amine salt known in the art.

As indicated above, particularly preferred substituents for R are p-nitrobenzyl, 4,5-dimethoxy-2-nitrobenzyl, and 1-(4-nitrophenyl)ethyl. Such derivatives of the compound of the present invention are particularly effective in treating cells in hypoxic regions of the tumor mass. These particular compounds have the potential to be activated under hypoxic conditions by a reductive mechanism whereby the lability of the carbamate moiety can be induced by the enzymatic conversion of the electron-withdrawing nitro group to the electron-releasing amino group.

The compounds of the invention have been found to be alkylating agents having antineoplastic activity in mice bearing the L1210 leukemia and to EMT6 mammary carcinoma cells in culture. These compounds display pronounced antitumor activity.

The compounds of the invention are preferably administered internally, e.g., intravenously, in the form of conventional pharmaceutical preparations, for example in conventional enteral or parenteral pharmaceutically acceptable excipients containing organic and/or inorganic inert carriers, such as water, gelatin, lactose, starch, magnesium stearate, talc, plant oils, gums, alcohol, Vaseline, or the like. The pharmaceutical preparations can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

The pharmaceutical preparation of the invention should include an amount of the compound of the invention effective for antineoplastic activity. The effective dosage will depend on the antineoplastic activity and toxicity of the particular compound employed and is thus within the ordinary skill of the art to determine for any particular host mammal or other host organism. Suitable dosages may be, for example, in the range of about 0.5–15 mg per kg for a human being. Alternatively, the claimed compounds may be used to control proliferation of neoplastic cells in vitro or they may be used as antineoplastic agents in nonhuman mammals.

The present invention is further described in detail by means of the following Examples. All parts and percentages are by weight unless explicitly stated otherwise. Melting points were determined with a Thomas-Hoover melting point apparatus and are uncorrected. $^1$H NMR spectra were recorded on a Varian EM-390 spectrometer with tetramethylsilane as an internal standard. Elemental analyses (C, H, N) were performed by the Baron Consulting Co., Orange, Conn. and were within ±0.5% of the calculated values for all compounds reported except compounds 10h (C: calculated, 33.5; found 34.2) and 12 (C: calculated, 34.3, found 34.9).

EXAMPLES 1–4

Synthesis of 2-alkoxycarbonyl and 2-aryloxycarbonyl -1,2-bis(methylsulfonyl)-1-methylhydrazines Example 1

1,2-Bis(methylsulfonyl)-2-(methoxycarbonyl)-1-methylhydrazine (compound 6) was synthesized as follows: A mixture of 1,2-bis(methylsulfonyl)-1-methylhydrazine (Shyam et al., J. Med. Chem. 30 2157–2161 (1987)) (1.00 g, 0.005 mol), anhydrous sodium carbonate (1.9 g, 0.018 mol), methyl chloroformate (1.23 g, 0.013 mol) and acetone (30 ml) was heated under reflux for 18 hr. The reaction mixture was filtered and the filtrate evaporated to dryness in vacuo. The residue, a thick oil, was stirred with methanol (5 ml) and cooled in ice. The solid that separated was filtered and recrystallized from ethanol-petroleum ether (0.63 g, 48.9%). The melting point (Mp) of this compound was found to be approximately 88–89° C. Analysis of the compound by $^1$H NMR (CDCl$_3$) showed the following results: δ 0 4.0(3H, s, OCH$_3$), 3.5, 3.4, 3.1 (9H, 3s, 2 CH$_3$SO$_2$ and NCH$_3$).

Example 2

1,2-Bis(methylsulfonyl)-2-(ethoxycarbonyl)-1-methylhydrazine (compound 7) was prepared from 1,2-bis(methylsulfonyl)-1-methylhydrazine and ethyl chloroformate using a procedure similar to that described for compound 6. The recrystallization solvent was ether-petroleum ether. Yield was 51.0%, and the Mp was approximately 89–90° C. $^1$H NMR (CDCl$_3$): δ 4.4 (2H, q, OCH$_2$), 3.5, 3.3 and 3.1 (9H, 3s, 2 CH$_3$SO$_2$ and NCH$_3$), 1.4 (3H, t, OCCH$_3$).

Example 3

1,2-Bis(methylsulfonyl)-2-(2-bromoethoxycarbonyl)-1-methylhydrazine (compound 8) was synthesized as follows: Triethylamine (1.45 g, 0.014 mol) was added in portions to a stirred solution of 1,2-bis(methylsulfonyl)-1-methylhydrazine (2.02 g, 0.01 mol) and 2-bromoethyl chloroformate (3.49 g, 0.019 mol) in acetone (100 ml) over a period of 15 min. The reaction mixture was stirred for an additional 18 hr, filtered, and the filtrate evaporated to dryness in vacuo. The residue was taken up in chloroform (100 ml) and washed with water (3×20 ml). The chloroform layer was dried over anhydrous magnesium sulfate, filtered, and the filtrate evaporated to dryness. The residue was triturated with petroleum ether until a solid separated. The solid was filtered and recrystallized from ethanol (1.52 g, 43.0%). Mp was approximately 81–82° C. $^1$H NMR (CDCl$_3$): δ 4.7 and 3.6 (4H, 2t, CH$_2$CH$_2$Br), 3.5, 3.3 and 3.1 (9H, 3s, 2CH$_3$SO$_2$ and NCH$_3$).

Example 4

1,2-Bis(methylsulfonyl)-2-[(4-methoxyphenoxy)carbonyl]-1-methylhydrazine (compound 9) was synthesized as follows: Triethylamine (0.269 g, 0.0029 mol) was added to a stirred solution of 1,2-bis(methylsulfonyl)-1-methylhydrazine (0.50 g, 0.0025 mol) and 4-methoxyphenyl chloroformate (0.63 g, 0.0033 mol) in acetone (30 ml) and the mixture stirred for 1 hr. The reaction mixture was filtered and the filtrate evaporated to dryness in vacuo. The residue was triturated with petroleum ether (5 ml) and the petroleum ether layer decanted. Column chromatography of the residue on silica gel (70–270 mesh, 60 Angstroms, CHCl$_3$), followed by crystallization from ethanol gave 0.14 g (16.1%) of the desired compound. Mp was approximately 101–102° C. $^1$H NMR (acetone-d$_6$) : δ 7.3 and 7.0 (4H, 2d, aromatic H), 3.9 (3H, s, OCH$_3$), 3.6, 3.4 and 3.2 (9H, 3s, 2 CH$_3$SO$_2$ and NCH$_3$).

EXAMPLES 5–24

Synthesis of 2-alkoxycarbonyl and 2-aryloxycarbonyl -1,2-bis(methylsulfonyl)-1-(2-chloroethyl)hydrazines 2-Alkoxycarbonyl- and 2-aryloxycarbonyl-1,2-bis(methylsulfonyl)-1-(2-chloroethyl)hydrazines may be prepared generally by reacting the appropriate alkyl or aryl chloroformate with 1,2-bis(methylsulfonyl)-1-(2-chloroethyl)hydrazine in an appropriate solvent in the presence of a base such as triethylamine (TEA) or anhydrous sodium carbonate as shown in Scheme 2.

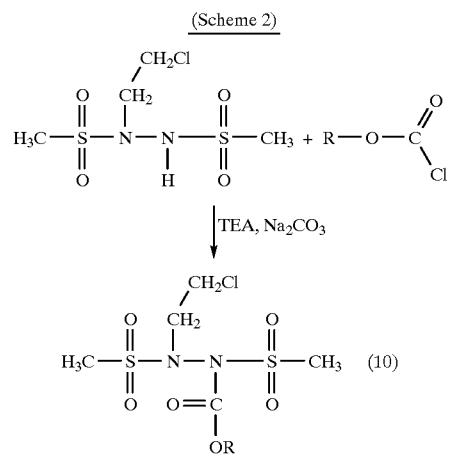

(Scheme 2)

Examples of substituents for R include methyl (compound 10a), 2-chloroethyl (compound 10b), vinyl (compound 10c), phenyl (compound 10d), p-tolyl (compound 10e), p-chlorophenyl (compound 10f), p-methoxyphenyl (compound 10g), or p-nitrobenzyl (compound 10h). These compounds may be synthesized as follows:

Example 5

1,2-Bis(methylsulfonyl)-1-(2-chloroethyl)-2-(methoxycarbonyl)hydrazine (compound 10a) may be synthesized as follows:. Triethylamine (1.45 g, 0.014 mol) was added to a stirred solution of compound 2 (Shyam et al., J. Med. Chem. 33 2259–2264 (1990))(1.25 g, 0.005 mol) and methyl chloroformate (2.46 g, 0.026 mol) in acetone (35 ml). The reaction mixture was stirred for an additional 16 hr, filtered, and the filtrate evaporated to dryness in vacuo. The residue was taken up in ethyl acetate (100 ml) and washed with water (3×15 ml). The ethyl acetate layer was dried over anhydrous magnesium sulfate, filtered, and the filtrate evaporated to dryness in vacuo. Column chromatography of the residue on silica gel (70–270 mesh, 60 Angstroms, CHCl$_3$), followed by crystallization from chloroform-petroleum ether gave 0.45 g (29.2%) of the desired compound. The Mp was approximately 87–88° C. $^1$H NMR (acetone-d$_6$): δ 4.0 (3H, s, OCH$_3$), 3.7–4.2 (4H, m, CH$_2$CH$_2$Cl), 3.5 and 3.3 (6H, 2s, 2 CH$_3$SO$_2$).

Example 6

1,2-Bis(methylsulfonyl)-1-(2-chloroethyl)-2-(2-chloroethoxycarbonyl)hydrazine (compound 10b) was synthesized as follows:. Triethylamine (1.20 g, 0.012 mol) was added to a stirred solution of compound 2 (1.25 g, 0.005 mol) and 2-chloroethyl chloroformate (1.00 g, 0.007 mol) in dry acetonitrile (10 ml). The reaction mixture was stirred for an additional 18 hr, filtered, and the filtrate evaporated to dryness in vacuo. The residue was triturated with petroleum ether (2×10 ml), and the petroleum ether layer was decanted each time. The residue was taken up in ethyl acetate (100 ml) and washed with dilute hydrochloric acid (3×10 ml), followed by water (2×10 ml). The ethyl acetate layer was dried over anhydrous magnesium sulfate, filtered, and the filtrate evaporated to dryness on a rotary evaporator. Column chromatography of the residue on silica gel (70–270 mesh, 60 Angstroms, CHCl$_3$), followed by crystallization from chloroform-petroleum ether gave 0.58 g (32.5%) of the desired compound. The Mp was approximately 73–74° C. $^1$H NMR (CDCl$_3$): δ 8 4.6 (2H, t, OCCH$_2$Cl), 3. 6–4.1 (6H, m, OCH$_2$ and NCH$_2$CH$_2$Cl), 3.5 and 3.2 (6H, 2s, 2 CH$_3$SO$_2$).

Example 7

1,2-Bis(methylsulfonyl)-1-(2-chloroethyl)-2-(vinyloxycarbonyl)hydrazine (compound 10c) was prepared by reacting compound 2 with vinyl chloroformate using a procedure similar to that described for compound 10b. The product was recrystallized from ethanol, and the yield was about 39.4% by weight. The Mp of the product was approximately 85–86° C. $^1$H NMR (CDCl$_3$): δ 7.0–7.3 (1H, m, CH=C), 4.8–5.3 (2H, m, C=CH$_2$), 3.6–4.2 (4H, m, CH$_2$CH$_2$Cl), 3.5 and 3.2 (6H, 2s, 2 CH$_3$SO$_2$).

Example 8

1,2-Bis(methylsulfonyl)-1-(2-chloroethyl)-2-(phenoxycarbonyl)hydrazine (compound 10d) was prepared by reacting compound 2 with phenyl chloroformate using a procedure similar to that described for compound 10d. However, the reaction time was decreased from 18 hr to 3 hr. The product was recrystallized from ethanol, and the yield was about 27.0% by weight. The Mp was approximately 75–76° C. $^1$H NMR (CDCl$_3$): δ 7.1–7.6 (5H, m, aromatic H), 3.6–4.2 (4H, m, CH$_2$CH$_2$Cl), 3.5 and 3.2 (6H, 2s, 2 CH$_3$SO$_2$).

Example 9

1,2-Bis(methylsulfonyl)-1-(2-chloroethyl)-2-[(4-tolyloxy)carbonyl]hydrazine (compound 10e) was prepared by reacting compound 2 with 4-tolyl chloroformate using a procedure similar to that employed for compound 10d. The product was recrystallized from ethanol, and the yield was about 31.2% by weight. The Mp was approximately 85–86° C. $^1$H NMR (CDCl$_3$): δ 7.3 and 7.1 (4H, 2d, aromatic H), 3.7–4.2 (4H, m, CH$_2$CH$_2$Cl), 3.5 and 3.2 (6H, 2s, 2 CH$_3$SO$_2$), 2.4 (3H, s, ArCH$_3$).

Example 10

1,2-Bis(methylsulfonyl)-1-(2-chloroethyl)-2-[(4-chlorophenoxy)carbonyl]hydrazine (compound 10f) was prepared by reacting compound 2 with 4-chlorophenyl chloroformate using a procedure similar to that employed for compound 10d. The product was recrystallized from ethanol, and the yield was about 54.4% by weight. The Mp was approximately 124–125° C. $^1$H NMR (acetone-d$_6$): δ 7.5 and 7.3 (4H, 2d, aromatic H), 3.9–4.2 (4H, m, CH$_2$CH$_2$Cl), 3.6 and 3.3 (6H, 2s, 2 CH$_3$SO$_2$).

Example 11

1,2-Bis(methylsulfonyl)-1-(2-chloroethyl)-2-[(4-methoxyphenoxy)carbonyl]hydrazine (compound 10g) was prepared by reacting compound 2 with 4-methoxyphenyl chloroformate using a procedure similar to the one employed for compound 10d. The product was recrystallized from ethanol, and the yield was about 30.0% by weight. The Mp of the product was approximately 119–121° C. $^1$H NMR (CDCl$_3$): δ 7.1 and 6.9 (4H, 2d, aromatic H), 3.6–4.2 (4H, m, CH$_2$CH$_2$Cl), 3.8 (3H, s, OCH$_3$), 3.5 and 3.2 (6H, 2s, 2 CH$_3$SO$_2$).

Example 12

1,2-Bis(methylsulfonyl)-1-(2-chloroethyl)-2-[(4-nitrobenzyloxy)carbonyl]hydrazine (compound 10h) was prepared by reacting compound 2 with 4-nitrobenzyl chloroformate using a procedure similar to that employed for compound 10d. The product was recrystallized from ethanol, and the yield was approximately 22.9% by weight. The Mp was approximately 132–133° C. $^1$H NMR (acetone-d$_6$): δ 8.3 and 7.8 (4H, 2d, aromatic H), 5.6 (2H, s, ArCH$_2$), 3.6–4.2 (4H, m, CH$_2$CH$_2$Cl), 3.6 and 3.3 (6H, 2s, 2 CH$_3$SO$_2$).

Example 13

2-Benzyloxycarbonyl-1,2-bis(methylsulfonyl)-1-(2-chloroethyl)hydrazine (compound 11) was prepared by reacting benzyl chloroformate with compound 2 using a procedure similar to that described for compound 10d. The compound was isolated as a thick oil in a yield of approximately 41.3% by weight. $^1$H NMR (acetone-d): δ 7.2–7.6 (5H, m, aromatic H), 5.4 (2H, s, ArCH$_2$), 3.5–4.0 (4H, m, CH$_2$CH$_2$Cl), 3.4 and 3.1 (6H, 2s, 2 CH$_3$SO$_2$).

Example 14

1,2-Bis(methylsulfonyl)-1-(2-chloroethyl)-2-[(4,5-dimethoxy-2-nitrobenzyloxy)carbonyl]hydrazine (compound 12) was prepared by reacting 4,5-dimethoxy-2-nitrobenzyl chloroformate with compound 2 using a procedure similar to that described for compound 10d. The product was recrystallized from ethanol, and the Mp was about 154° C. Yield was about 17.6% by weight. $^1$H NMR (acetone d$_6$): δ 7.7 and 7.4 (2H, 2s, aromatic H), 5.8 (2H, d, ArCH$_2$), 3.7–4.1 (4H, m, CH$_2$CH$_2$Cl), 3.9–4.0 (6H, 2s, 2 OCH$_3$), and 3.5 and 3.2 (6H, 2s, 2 CH$_3$SO$_2$).

Example 15

1,2-Bis(methylsulfonyl)-1-(2-chloroethyl)-2-[(2-nitrobenzyloxy)carbonyl]hydrazine (compound 13a) was prepared as follows: A solution of 2-nitrobenzyl alcohol (2.0 g, 0.013 mol) in dry dioxane (5 ml) was added to a stirred solution of phosgene in toluene (20% w/v, 20 ml) at −15° C. The mixture was then stirred at room temperature for 24 hr. The reaction mixture was evaporated to dryness in vacuo at <40° C. To the residue was added anhydrous acetonitrile (15 ml), followed by compound 2 (1.0 g, 0.004 mol) and triethylamine (1.3 ml, 0.009 mol). The reaction mixture was stirred for 16 hr at 0–5° C. and evaporated to dryness on a rotary evaporator. The residue was stirred with ethyl acetate (150 ml) for 10 min. The mixture was washed with 2×15 ml of hydrochloric acid (5% w/v). The ethyl acetate layer was dried over anhydrous magnesium sulfate, filtered, and the filtrate evaporated to dryness on a rotary evaporator. Column chromatography on silica gel (70–270 mesh, 60 Angstroms, chloroform), followed by recrystallization from ethanol gave 0.48 g (28.1% by weight) of the desired compound. The melting point was determined to be about Mp 111–113° C. $^1$H NMR (acetone-d$_6$): δ 8.1 and 7.5–8.0 (4H, d, m, aromatic H), 5.8 (2H, d, ArCH$_2$), 3.6–4.1 (4H, m, CH$_2$CH$_2$Cl), 3.5 and 3.2 (6H, 2s, 2 CH$_3$SO$_2$).

Example 16

1,2-Bis(methylsulfonyl)-1-(2-chloroethyl)-2-[(4-chloro-2-nitrobenzyloxy)carbonyl]hydrazine (compound 13b) was prepared from 4-chloro-2-nitrobenzyl alcohol using a procedure similar to that described for compound 13a. The Mp was about 120–121° C., and the yield was approximately 40.0% by weight after recrystallization from ethanol. $^1$H NMR (acetone-d$_6$): δ 8.2 and 7.7–8.0 (3H, s, m, aromatic H), 5.8 (2H, d, ArCH$_2$), 3.6–4.1 (4H, m, CH$_2$CH$_2$Cl), 3.5 and 3.2 (6H, 2s, 2 CH$_3$SO$_2$).

Example 17

1,2-Bis(methylsulfonyl)-1-(2-chloroethyl)-2-[(5-chloro-2-nitrobenzyloxy)carbonyl]hydrazine (compound 13c) was prepared from 5-chloro-2-nitrobenzyl alcohol using a procedure similar to that described for compound 13a. The Mp was approximately 100–102° C., and the yield was approximately 14.6% by weight after recrystallization from ethanol. $^1$H NMR (acetone-d$_6$): δ 8.2, 8.0 and 7.7 (3H, 2d, s, aromatic H), 5.8 (2H, d, ArCH$_2$), 3.6–4.1 (4H, m, CH$_2$CH$_2$Cl), 3.5 and 3.2 (6H, 2s, 2 CH$_3$SO$_2$).

Example 18

1,2-Bis(methylsulfonyl)-1-(2-chloroethyl)-2-[(3-methoxy-4-nitrobenzyloxy)carbonyl]hydrazine (compound 13d) was prepared from 3-methoxy-4-nitrobenzyl alcohol using a procedure similar to that described for compound 13a. The Mp was determined to be about 56–57° C., and the yield was about 29.4% by weight after recrystallization from ethanol. $^1$H NMR (acetone d$_6$): δ 7.8, 7.5 and 7.2 (3H, 2d, s, aromatic H), 5.8 (2H, d, ArCH$_2$), 3.6–4.1 (4H, m, CH$_2$CH$_2$Cl), 4.0 (3H, S, OCH$_3$), 3.6 and 3.3 (6H, 2s, 2 CH$_3$SO$_2$).

Example 19

1,2-Bis(methylsulfonyl)-1-(2-chloroethyl)-2-[(5-methyl-2-nitrobenzyloxy)carbonyl]hydrazine (compound 13e) was prepared from 5-methyl-2-nitrobenzyl alcohol using a procedure similar to that described for compound 13a. The Mp was found to be 112–113° C., and the yield was about 24.3% by weight after recrystallization from ethanol. $^1$H NMR (acetone-d$_6$): δ 8.1, 7.8 and 7.4 (3H, 2d, s, aromatic H), 5.8 (2H, d, ArCH$_2$), 3.6–4.1 (4H, m, CH$_2$CH$_2$Cl), 3.6 and 3.3 (6H, 2s, 2 CH$_3$SO$_2$), 2.5 (3H, s, ArCH$_3$).

Example 20

1,2-Bis(methylsulfonyl)-1-(2-chloroethyl)-2-[[1-(4-nitrophenyl)ethoxy]carbonyl]hydrazine (compound 14) was prepared as follows: 1-(4-Nitrophenyl)ethanol was prepared using a procedure analogous to that reported in the literature for the synthesis of 3-nitrobenzyl alcohol from 3-nitrobenzaldehyde (Furniss, B. S., Hannaford, A. J., Rogers, V., Smith, P. W. G., and Tatchell, A. R. Cognate preparation: m-nitrobenzyl alcohol. In: Vogel's Textbook of Practical Organic Chemistry, 4th ed., Longman, London, p. 357 (1978)). Briefly, 4-nitroacetophenone (15.1 g) was dissolved in methanol (300 ml) and was converted to 1-(4-nitrophenyl)ethanol (13.2 g) by reduction with sodium borohydride (1.4 g) in 0.2 M aqueous sodium hydroxide (25 ml). A solution of 1-(4-nitrophenyl)ethanol (2.4 g, 0.014 mol) in tetrahydrofuran (5 ml) was added dropwise to a stirred, ice-cold solution of phosgene in toluene (20% w/v, 30 ml). The flask was then wrapped in aluminum foil, allowed to equilibrate to room temperature, and the reaction mixture was stirred for an additional 24 hr. A dark oil was obtained following evaporation of the reaction mixture in vacuo at a temperature not exceeding 30° C. To this oil was added anhydrous acetonitrile (20 ml) and compound 2 (1.5 g, 0.006 mol). After cooling this mixture in an ice bath, triethylamine (1.7 ml, 0.012 mol) was added dropwise and the reaction mixture stirred for 17 hr at 4° C. The reaction mixture was evaporated on a rotary evaporator at a temperature not exceeding 30° C. The residue was taken up in ethyl acetate (150 ml) and washed with 2×50 ml and 1×100 ml of hydrochloric acid (5% w/v). The combined aqueous layers were extracted with ethyl acetate (50 ml) and the extract combined with the organic (ethyl acetate) layer from the previous extraction step. The combined ethyl acetate layers were washed with brine (100 ml), dried over anhydrous magnesium sulfate and filtered. The filtrate was evaporated to dryness to give a viscous oil. The desired compound was obtained by column chromatography on silica gel (70–270 mesh, 60 Angstroms, chloroform-methylene chloride), followed by recrystallization from ethanol. The yield was about 35.0% by weight. The Mp was about 94–95° C. $^1$H NMR (acetone-d$_6$): δ 8.3 and 7.8 (4H, 2d, aromatic H), 6.2 (lH, m, ArCH), 3.6–4.1 (4H, m, CH$_2$CH$_2$Cl), 3.5 and 3.2 (6H, 2s, 2 CH$_3$SO$_2$), 1.7 (3H, dd, C—CH$_3$).

Example 21

O-Dibenzylphosphate-methyl carbamate (compound 15) was prepared as follows:
(A) Preparation of O-chloromethyl-S-butylthiocarbonate A solution of 1-butanethiol (BUSH) (12.1 ml, 113.6 mmol) and triethylamine (15.75 ml, 113.6 mmol) in diethyl ether (45 ml) was added to a diethyl ether solution (220 ml) of chloromethyl chloroformate (10.0 ml, 113.6 mmol) at 0° C. over 30 min. The reaction mixture was stirred at 0° C. for an additional 30 min., and then at room temperature for 48 hr. The product was filtered and concentrated to give a crude oily product, which was used directly for the next reaction.
(B) Preparation of O-iodomethyl-S-butylthiocarbonate:

The crude product of (A) above was dissolved in acetone (140 ml), and NaI (24.8 g, 165 mmol) was added. The reaction mixture was heated at 40° C. for 3 hr. The reaction mixture was then filtered and the insoluble material was rinsed with acetone and ether. The filtrate was evaporated and the residue partitioned between pentane (300 ml) and water (100 ml). The organic layer was washed with 5% NaHCO$_3$ (50 ml), saturated Na$_2$S$_2$O$_3$ (50 ml) and water (2×50 ml). The resulting organic layer was dried, filtered and evaporated to give 22.8 g (76%) of the desired product as a colorless liquid.
(C) Preparation of O-dibenzylphosphate-S-butylthiocarbonate:

A tetrahydrofuran (THF) solution (20 ml) of the crude product made in (B) above (11.0 g, ~40 mmol) was added to a THF solution (100 ml) of tetrabutylammonium dibenzylphosphate (prepared via the reaction of tetrabutylammonium hydroxide and dibenzyl phosphate) at 0° C. The resulting solution was stirred at room temperature for 24 hr. The reaction mixture was filtered through a pad of Celite, and the filtrate was concentrated and chromatographed (10–20% ethyl acetate/hexanes) to afford 8.5 g (50%) of the desired product.

(D) Preparation of O-dibenzylphosphate-methyl chloroformate:

A dichloromethane solution (25 ml) of the thiocarbonate made in (C) above (2.67 g, 6.30 mmol) was treated with $SO_2Cl_2$ (0.60 ml, 7.56 mmol) at −40° C. The reaction mixture was stirred at room temperature for 3 hr. The solvent was removed in vacuo. The resulting crude product was dried under high vacuum for 1 hr, and then used for next reaction without further purification.

To an acetone solution (7.9 ml) of the crude chloroformate made in (D) above (~6.30 mmol) was added (at 0° C.) diisopropylethylamine ($EtPr_2N$) (1.10 ml, 6.30 mmol), followed by an acetone solution of the parent compound, 1,2-bis(methylsulfonyl)-1-(2-chloroethyl)hydrazine (1.05 g, 4.20 mmol). The reaction was warmed to room temperature, and the stirring was maintained at room temperature for 15 hr. At this point, the solvent was partially removed in vacuo, and the reaction mixture was diluted with ethyl acetate (100 ml), and then washed with brine (2×15 ml). The organic phase was dried and concentrated in vacuo. The residue was purified with silica gel chromatography (40–50% ethyl acetate/hexanes) to provide 2.0 g (82%) of the protected O-dibenzylphosphate-methyl carbamate. $^1$H NMR (300 MHz, $CDCl_3$): δ 7.40 (m, 10H), 5.82–5.60 (m, 2H), 5.10 (m, 4H), 3.84 (m, 2H), 3.64 (m, 2H), 3.40 (s, 3H), 3.13 (S, 3H). FAB HRMS calcd. for $C_{20}H_{27}ClN_2O_{10}S_2P$ (MH$^+$) : 585.0533; found: 585.0533.

Example 22

Preparation of free-phosphoric acid of O-dibenzylphosphate-methyl carbamate

The free-phosphoric acid of O-dibenzylphosphate-methyl carbamate (compound 15) was synthesized as follows:

O-Dibenzylphosphate-methyl carbamate (2.77 g, 4.74 mmol) was dissolved in ethyl acetate (60 ml). To this solution was added palladium on carbon (1.0 g, 10% palladium content, 0.95 mmol). The resulting mixture was subjected to hydrogenation at 30 psi pressure for 15 hr at room temperature. The reaction mixture was filtered through a pad of Celite with rinsing (ethyl acetate). The combined filtrates were concentrated in vacuo to provide ~1.92 g (100%) of the desired free acid having the formula

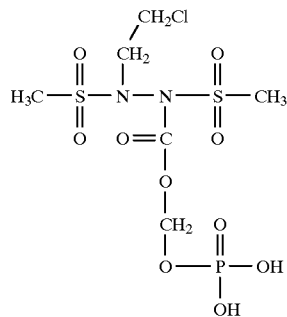

$^1$H NMR (300 MHz, Acetone-$d_6$) : δ 6.10–5.70 (bs, 2H), 3.95 (m, 2H), 3.78 (m, 2H), 3.55 (s, 3H), 3.26 (s, 3H). LRMS (EI) calcd. for $C_6H_{15}ClN_2PO_{10}S_2$ (MH$^+$) : 405, found: 405.

Example 23

Preparation of the triethanolamine salt and the triethylamine salt of the free acid acid of O-dibenzylphosphate-methyl carbamate:

The triethanolamine salt of the free acid acid of O-dibenzylphosphate-methyl carbamate was synthesized as follows: To an oily ethyl acetate solution (2 ml) of the free acid compound made in Example 22 (946 mg, 2.34 mmol) was added (at 0° C.) 0.1 M triethanolamine in ethyl acetate (23.4 ml, 2.34 mmol). The reaction was stirred at 0° C. for 1 hr and kept at −20° C. overnight. The white precipitate that formed was collected by filtration and washed with cooled ethyl acetate. The sticky solids obtained were dried at high vacuum for 1 hr to provide 900 mg (70%) of the crude triethanolamine adduct (compound 16).

The triethylamine salt of the free acid acid of O-dibenzylphosphate-methyl carbamate was synthesized as follows: To an ethyl acetate solution (14 ml) of the free acid compound made in Example 22 above (960 mg, 2.37 mmol) was added an ethyl acetate solution (10 ml) of triethylamine (0.33 ml, 2.37 mmol) at 0° C. The reaction was stirred at 0° C. for 1 hr and kept at −20° C. for 15 hr. The solvent was then removed and the oily residue was dried under high vacuum for 1 hr to provide 910 mg (76%) of the crude triethylamine adduct (compound 17).

Example 24

The compound of the formula

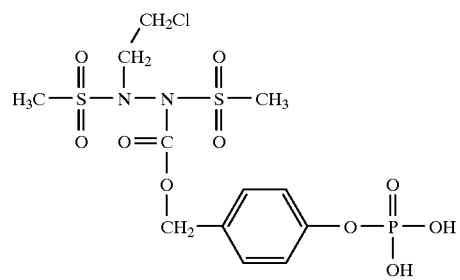

was prepared as follows:

(A) Diethylphosphatebenzyl alcohol (5.00 g, 40.32 mmol) was dissolved in anhydrous acetonitrile (160 ml), and the resulting solution was cooled to −10° C. To this solution was then added $CCl_4$ (19.45 ml, 201.60 mmol), followed by $EtPr_2N$ (14.76 ml, 84.67 mmol) and 4-dimethylaminopyridine (DMAP) (492 mg, 4.03 mmol). One minute later, neat diethyl phosphite (7.54 ml, 58.46 mmol) was added dropwise to the above solution at −10° C. The reaction was stirred at −10° C. for 1 hr and then at room temperature overnight. The reaction was quenched with 0.5 M $KH_2PO_4$ (100 ml). The solvent was then partially removed in vacuo. The resulting reaction mixture was extracted with ethyl acetate (3×100 ml). The combined extracts were washed with water and brine, and then dried with $Na_2SO_4$. Filtration and evaporation of the organic layer gave a yellowish crude product (~11 g, ~100%), which was used in the next reation without purification.

(B) To a dichloromethane solution (15 ml) of the product made in (A) above (736 mg, 2.83 mmol) was added at 0° C. p-nitrophenylchloroformate (684 mg, 3.40 mmol), followed by $EtPr_2N$ (0.59 ml, 3.40 mmol). The reaction was stirred at 0° C. for 1 hr and then at room temperature overnight. At this point, the reaction mixture was diluted with dichloromethane (75 ml), and then washed with $H_2O$ (15 ml) and brine (15 ml). The resulting organic layer was dried and concentrated in vacuo. The residue was chromatographed (40–60% ethyl acetate in hexanes) to provide 800 mg (67%) of the desired product as a pale yellow oil. $^1$H NMR (300 MHz, $CDCl_3$) : δ 8.26–8.22 (d, 2H), 7.39–7.24 (m, 6H), 5.23

(s, 2H), 4.20 (m, 4H), 1.34 (m, 6H). FAB HRMS calcd. for $C_{18}H_{21}NO_9P$ ($MH^+$) : 426.0954; found: 426.0954.

(C) To an acetone solution (12 ml) of the product made in (B) above (800 mg, 1.88 mmol) was added at 0° C. ethyl acetate (0.36 ml, 2.078 mmol). This was followed by slow addition of an acetone solution (4 ml) of the parent alkylating agent, 1,2-bis(methylsulfonyl)-1-(2-chloroethyl) hydrazine (566 mg, 2.26 mmol). Stirring was continued at 0° C. for 1 hr. At this point, a catalytic amount of DMAP was added, and the reaction mixture was stirred at room temperature for 12 hr. The solvent was removed in vacuo, and the residue was taken up in ethyl acetate (100 ml). The resulting solution was washed with brine (2×15 ml), and the organic layer was dried and concentrated in vacuo. The residue was chromatographed (40–60–70% ethyl acetate in hexanes) to provide 669 mg (66%) of the desired product as a clear oil.

(D) To an acetonitrile solution (50 ml) of the compound made in (C) above (1.36 g, 2.53 mmol) was added at 0° C. 2,4-lutidine (1.46 ml, 12.66 mmol), followed by slow addition of neat trimethylsilyl bromide (TMSBr) (1.67 ml, 12.66 mmol). The reaction mixture was stirred at 0° C. for 1 hr and then at room temperature overnight. The solvent was removed in vacuo (with dry-ice trap), and the resulting yellowish residue was co-evaporated with aceonitrile (2×25 ml). The resulting pale yellow residue was then co-evaporated with methanol (25 ml). The resulting oily residue was then subjected to silica gel chromatography (ethyl acetate to $CH_3CN$ to 10% $H_2O$ in $CH_3CN$) to provide 1.08 g (89%) of the desired phosphoric acid-lutidine salt of

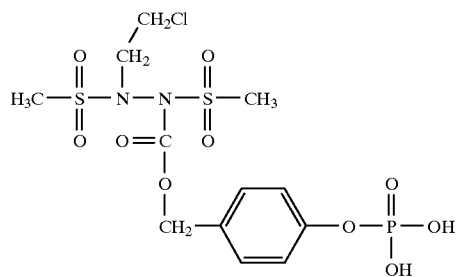

(compound 18) as a white solid.

$^1$H NMR (300 MHz, DMSO-$d_6$): δ 8.32 (d, J=s.5.11 Hz, 1H), 7.38 (d, J=8.7 Hz, 2H), 7.21–7.13 (m, 4H), 5.27 (s, 2H), 3.87–3.80 (m, 2H), 3.70–3.67 (m, 2H), 3.49 (s, 3H), 3.18 (s, 3H), 2.44 (s, 3H), 2.30 (s, 3H).

Activation of 2-alkoxycarbonyl and 2-aryloxycarbonyl -1,2-bis(methylsulfonyl)-1-(2-chloroethyl)hydrazines Table 3 shows the rates of activation of 2-alkoxycarbonyl- and 2-aryloxycarbonyl-1,2-bis(methylsulfonyl)-1-(2-chloroethyl)hydrazines (compounds 10a–h) under different conditions. The rates of activation of compounds 10a–h were measured in 1 mM phosphate buffer (pH 7.4, 37° C.) alone, 1 mM phosphate buffer containing 5 mM GSH (pH 7.4, 37° C.), and in 1 mM phosphate buffer containing 5 mM GSH and 17.5 U/ml of GST (pH 7.4, 37° C.) (Table 3). The rates of activation by hydrolysis, thiolysis and GST-catalyzed thiolysis were calculated from these data.

TABLE 3

| | Calculated Activation Rates, nmole/ml/min, due to | | |
|---|---|---|---|
| Compound No. | Hydrolysis | Thiolysis (5 mM GSH) | Catalyzed Thiolysis (5 mM GSH + 17.5 U/ml GST) |
| 10a | 0.03 | 0.02 | 0.00 |
| 10b | 0.02 | 0.02 | 0.08 |
| 10c | 0.07 | 2.07 | 4.70 |
| 10d | 0.06 | 0.37 | 1.80 |
| 10e | 0.02 | 0.45 | 1.52 |
| 10f | 0.06 | 0.92 | 5.33 |
| 10g | 0.14 | 0.41 | 1.80 |
| 10h | not detected | 0.06 | 20.5 |

In general, the activation rate followed the rank order, hydrolysis (i.e., buffer alone)<thiolysis (i.e., GSH alone) <thiolysis catalyzed by GST. Compound 10h is shown to undergo little or no hydrolysis in phosphate buffer at physiological pH and an extremely slow rate of thiolysis when reacted with GSH. However, a relatively high rate of activation occurs when thiolysis is catalyzed by GST.

Antitumor Activity of 2-alkoxycarbonyl and 2-aryloxycarbonyl -1,2-bis(methylsulfonyl)-1-(2-chloroethyl)hydrazines The ascites cell form of leukemia L1210 was obtained from the Frederick Cancer Research Facility, Division of Cancer Treatment Tumor Repository of the National Cancer Institute, and was maintained by serial passage in tissue culture. Every 8 weeks, tumor cells were injected intraperitoneally into 5 donor $CD_2F_1$ mice 8–10 weeks of age and were allowed to grow for 7 days. The peritoneal fluid was withdrawn, and the suspension was centrifuged for 5 min at 1600×g. The supernatant was decanted, and $10^5$ cells/ml were seeded into 10 ml of RPMI 1640 medium supplemented with 10% fetal bovine serum and 1% L-glutamine (200 mM) and once again maintained in culture. To assay for antitumor activity, 0.1 ml of the cell suspension containing $10^5$ leukemia cells was injected into each recipient mouse. Test compounds were administered over a wide range of dosage levels (12.5–60 mg/kg), beginning 24 hr after tumor implantation, and continued once daily for 6 consecutive days. Each drug was administered intraperitoneally as a solution in 100% dimethyl sulfoxide, in a volume not exceeding 25 μl. In each experiment, animals were distributed into groups of 5 mice of comparable weight and maintained throughout the course of the experiment on Purina Laboratory Chow pellets and water ad libitum. Control tumor-bearing mice given comparable volumes of vehicle were included in each experiment. Mice were weighed during the course of the experiments, and the percentage change in body weight from onset to termination of therapy was used as an indication of drug toxicity. Determination of the sensitivity of neoplasms to these agents was based upon the prolongation of survival time afforded by the drug treatments.

The antitumor activity of compounds 10a–h and 16 were assessed in mice bearing the L1210 leukemia. The results of these tests are summarized in Tables 4 and 5 which show the effects of 2-alkoxycarbonyl- and 2-aryloxycarbonyl-1,2-bis(methylsulfonyl)-1-(2-chloroethyl)hydrazines on the survival time of mice bearing the L1210 leukemia.

TABLE 4

| Compound | Optimum Daily Dose (mg/kg) | Av Δ wt (%) | % T/C | % 60-day survivors |
|---|---|---|---|---|
| 10a | 60 | −10.9 | 200 | — |
| 10b | 25 | −10.7 | 189 | — |
| 10c | 12.5 | −12.4 | 127 | — |
| 10d | 30 | −1.0 | 234 | 40 |
| 10e | 30 | −3.0 | 235 | 20 |
| 10f | 30 | −1.1 | 75 | 80 |
| 10g | 30 | −2.5 | 304 | 40 |
| 10h | 30 | −8.6 | 222 | — |

TABLE 5

| Compound | Multiple Dose (mg/kg) | Average Survival (Days) | T/C (%) | % Body Weight Change | Long Term Survival |
|---|---|---|---|---|---|
| 16 | none | 8.0 | — | +3.7 | 0/5 |
| 16 | 6 × 10 | 14.7 | 184 | −3.6 | 2/5 |
| 16 | 6 × 20 | 19.5 | 244 | +2.5 | 3/5 |
| 16 | 6 × 40 | — | — | +3.7 | 5/5 |
| 16 | 6 × 60 | 11.0 | 138 | −23.2 | 3/5 |

In Table 4, the optimum daily dose was administered once per day for six consecutive days, beginning 24 hours after tumor implantation, with 5–10 mice being used per group. In Table 5, multiple dosages of compound 16 are indicated. "Av Δ wt" refers to the average percent change in body weight from onset to termination of therapy. "% T/C" refers to the average survival time of treated/control mice×100. Cures (60-day survivors) are listed separately and are not included in this calculation.

Compounds 10a to 10h and 16 displayed significant activity against the L1210 leukemia tumor. Compounds 10d through 10g in which an aromatic ring was directly attached to the carbamate oxygen (R=aryl) produced the best results. The aromatic compounds 10d–g, were less toxic than the aliphatic analogs 10a–c, as evidenced by the major differences in the loss of host body weight produced by these two groups of compounds. As shown in Table 4, all of the aliphatic analogs produced body weight losses of >10.0% at their optimum daily dosage levels. Interposition of a methylene (—$CH_2$—) group between the aromatic ring and the carbamate nitrogen resulted in a slight lowering of antileukemic activity. Compound 10h produced a maximum %T/C of 222 at the optimum dosage level of 30 mg/kg per day for 6 consecutive days. As shown in Table 5, compound 16 also showed significant antitumor activity.

The ability of compounds 10h, 11, 12, and 14 to exert preferential toxicity to hypoxic cells was evaluated using the EMT6 mammary carcinoma by methodology described previously (Rockwell, S., Keyes, S. R., and Sartorelli, A. C. Rad. Res. 116: 100–113 (1988); Keyes, S. R., Rockwell, S., and Sartorelli, A. C. Cancer Res. 45: 213–216 (1985)). Briefly, exponentially growing monolayers of EMT6 (or CHO-K1/dhfr clone) were exposed to a continuously flowing 95% $N_2$/5% $CO_2$ humidified atmosphere for 2 h to produce radiobiologic hypoxia. Parallel flasks were maintained similarly in humidified 95% air/5% $CO_2$. Without breaking the hypoxia, cells were exposed to various concentrations of the test agent for 1 hr. Cell survival was then measured by colony formation.

CHO-K1/dhfr cells were used to examine the role of the reductive enzymes NADPH:cytochrome $P_{450}$ reductase and DT-diaphorase in the activation of compounds 10h and 12 in situ. Clones of CHO-K1/dhfr⁻ cells transfected with and overexpressing cDNAs for each of these enzymes were used for this purpose (Belcourt, M. F., Hodnick, W. F., Rockwell, S., and Sartorelli, A. C. Proc. Natl. Acad. Sci. USA 93: 456–460 (1996); Belcourt, M. F., Hodnick, W. F., Rockwell, S., and Sartorelli, A. C. Biochem. Pharmacol. 51: 1669–1678 (1996)).

The cytotoxicity of compound 10h was evaluated against EMT6 mouse mammary carcinoma cells in vitro under aerobic and hypoxic conditions using the colony-forming assay described above. FIG. 1 depicts the survival of EMT6 cells exposed to various concentrations of compound 10h for 1 hr under hypoxic or aerobic conditions in vitro. Points are the geometric means of two or more independent determinations of surviving fractions. The SEMs are shown where $n \geq 3$ and where the error is larger than the point size. Open triangles represent aerobic data points and filled triangles represent hypoxic data points. As shown in FIG. 1, at a concentration of 40 μM, a 1 hr exposure to compound 10h caused 2 logs of kill of hypoxic EMT6 cells, with relatively minor toxicity to corresponding aerobic cells.

Figure 2:
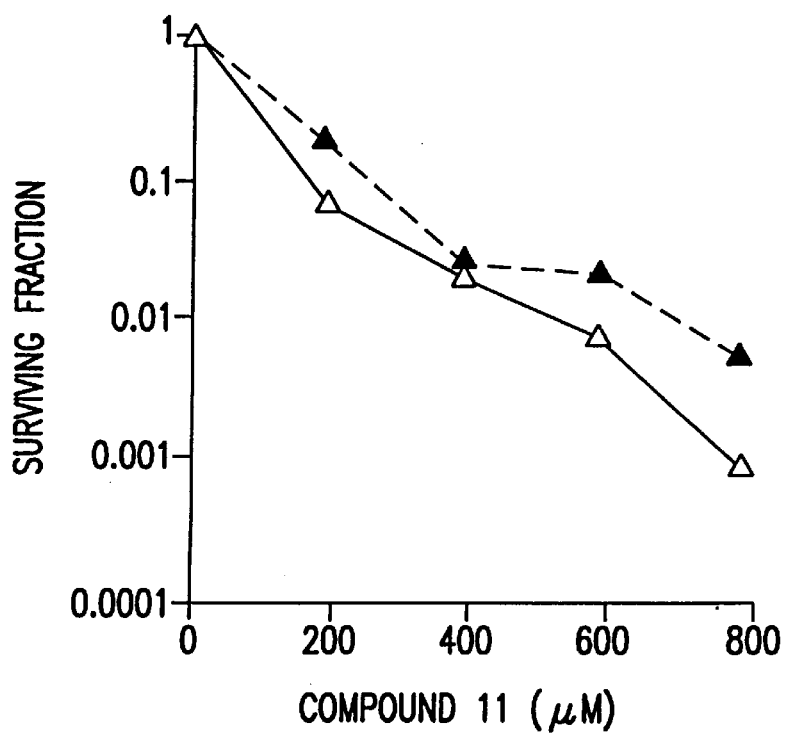
FIG. 2 is a graph of the survival of EMT6 cells exposed to various concentrations of compound 11 for 1 hr under hypoxic or aerobic conditions in vitro.

To ensure that the nitro group in compound 10h is important to the preferential cytotoxicity to hypoxic cells, the unsubstituted benzyl derivative (compound 11) was evaluated against EMT6 cells under aerobic and hypoxic conditions as outlined above. As shown in FIG. 2, compound 11 was essentially equitoxic to EMT6 cells under both conditions of oxygenation. This finding suggests the nitro group is essential for preferential toxicity to hypoxic cells.

Figure 3:
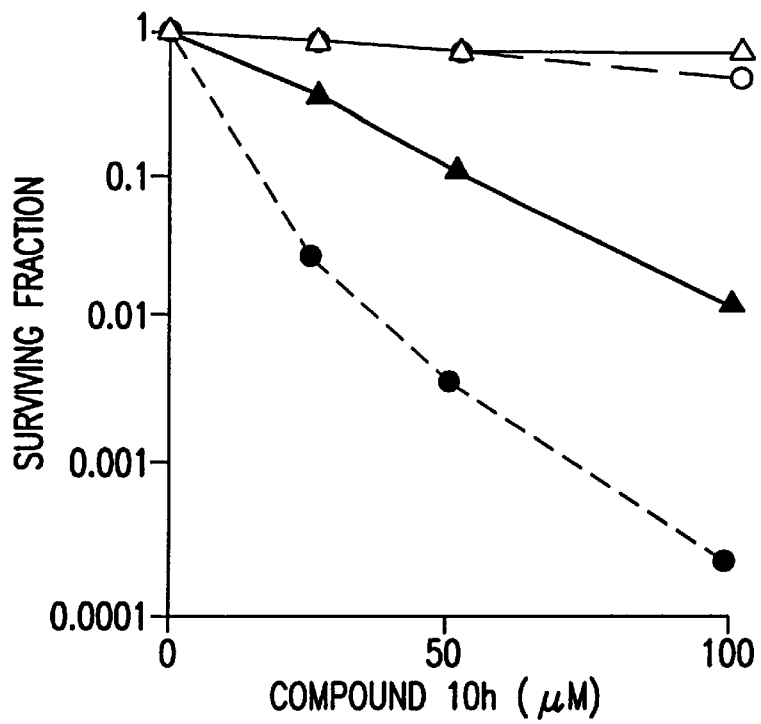
FIG. 3 is a graph of the cytotoxicity of compound 10h evaluated in aerobic and hypoxic Chinese hamster ovary (CHO-K1/dhfr⁻) cells transfected with and overexpressing cDNAs for NADPH:cytochrome $P_{450}$ reductase.
Figure 4:
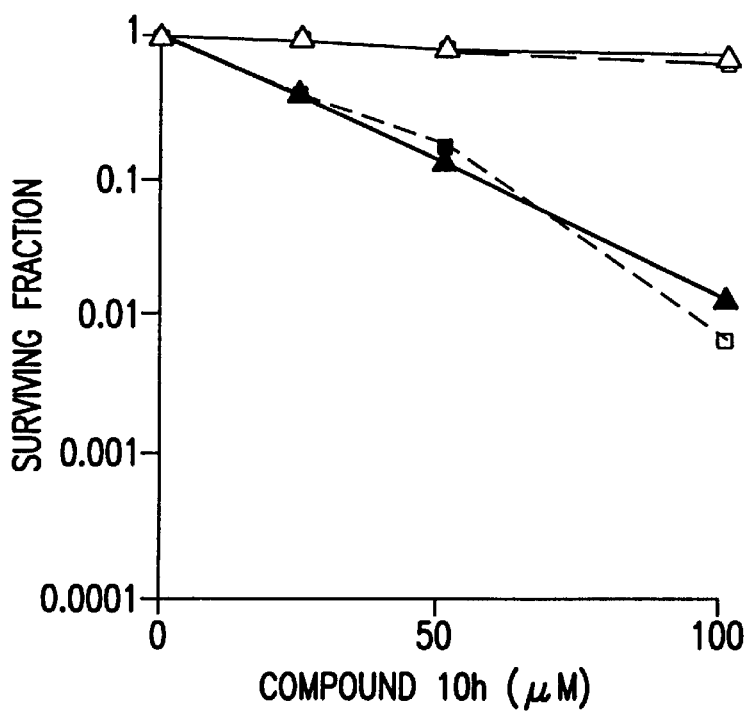
FIG. 4 is a graph of the cytotoxicity of compound 10h evaluated in aerobic and hypoxic Chinese hamster ovary (CHO-K1/dhfr⁻) cells transfected with and overexpressing cDNAs for DT-diaphorase.

The cytotoxicity of compound 10h was evaluated in aerobic and hypoxic Chinese hamster ovary (CHO-K1/dhfr⁻) cells transfected with and overexpressing cDNAs for NADPH:cytochrome $P_{450}$ reductase (27-fold more than parental cells, FIG. 3) or DT-diaphorase (133-fold more than parental cells, FIG. 4), two reductases with the potential to activate compound 10h. In FIGS. 3 and 4, points are means of duplicate determinations. Open triangles are parental-aerobic, filled triangles are parental-hypoxic, open circles are NADPH:cytochrome $P_{450}$ reductase-transfected-aerobic; filled circles are NADPH:cytochrome $P_{450}$ reductase-transfected-hypoxic; open squares are DT-diaphorase-transfected-aerobic; and filled squares are DT-diaphorase-transfected-hypoxic. As shown in FIGS. 3 and 4, CHO-K1/dhfr⁻ cells were less sensitive to compound 10h than EMT6 cells, and hypoxic CHO-K1/dhfr⁻ cells were more sensitive to compound 10h than their aerobic counterparts. Increased sensitivity to compound 10h occurred in cells overexpressing NADPH:cytochrome $P_{450}$ reductase, indicating that this enzyme was involved in bioactivating 10h in intact cells. In contrast, overexpression of DT-diaphorase did not result in an increase in the kill of either hypoxic or oxygenated cells, suggesting that DT-diaphorase was not involved in activating this compound.

Figure 5:
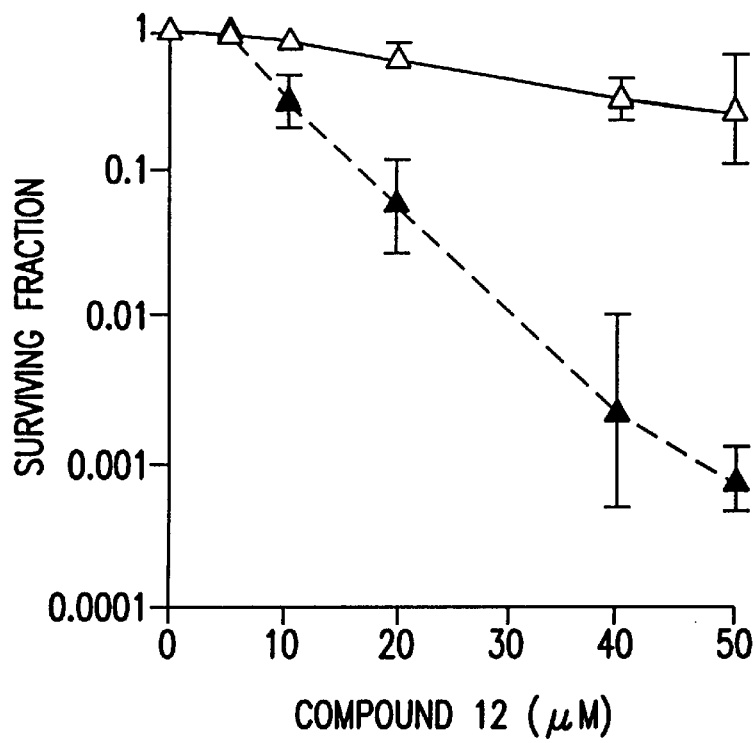
FIG. 5 is a graph showing survival of EMT6 cells exposed to various concentrations of compound 12 for 1 hr under hypoxic or aerobic conditions in vitro.
Figure 6:
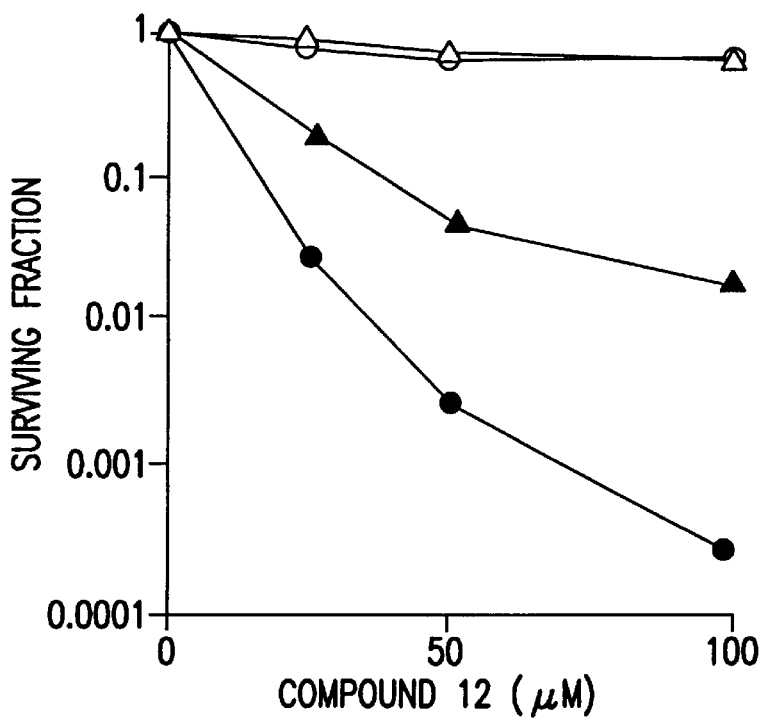
FIG. 6 is a graph showing survival of aerobic and hypoxic CHO-K1/dhfr⁻ cells and an NADPH:cytochrome $P_{450}$ reductase cDNA transfected clone exposed to various concentrations of compound 12 for 1 hr.

Compound 12 was evaluated for its ability to exert preferential toxicity to hypoxic EMT6 cells relative to their aerobic counterparts. FIG. 5 shows survival of EMT6 cells exposed to various concentrations of compound 12 for 1 hr under hypoxic or aerobic conditions in vitro. Points are geometric means of two or more independent determinations of surviving fractions. The SEMs are shown where $n \geq 3$ and where the error is larger than the point size. Open triangles are aerobic data points, and filled triangles are hypoxic data points. FIG. 6 shows survivals of aerobic and hypoxic CHO-K1/dhfr⁻ cells, NADPH:cytochrome $P_{450}$ reductase cDNA transfected clone expressing 27-fold more NADPH:cytochrome $P_{450}$ reductase than parental cells. Points are means of duplicate determinations. Open triangles are parental-aerobic; filled triangles are parental-hypoxic; open circles are NADPH:cytochrome $P_{450}$ reductase-transfected-aerobic; filled circles are NADPH:cytochrome $P_{450}$ reductase-transfected-hypoxic.

As shown in FIG. 5, at a concentration of 50 μM, a 1 hr exposure to compound 12 caused greater than 3 logs of kill of hypoxic EMT6 cells, with relatively minor toxicity to corresponding aerobic cells. An evaluation of the cytotoxicity of this agent to aerobic and hypoxic CHO-K1/dhfr⁻ cells (FIG. 6) yielded results similar to those described for compound 10h. Thus, compound 12 was >3000-times more cytotoxic to hypoxic CHO-K1/dhfr cells transfected with and overexpressing cDNAs for NADPH-cytochrome $P_{450}$ reductase than to their aerobic counterparts.

Figure 7:
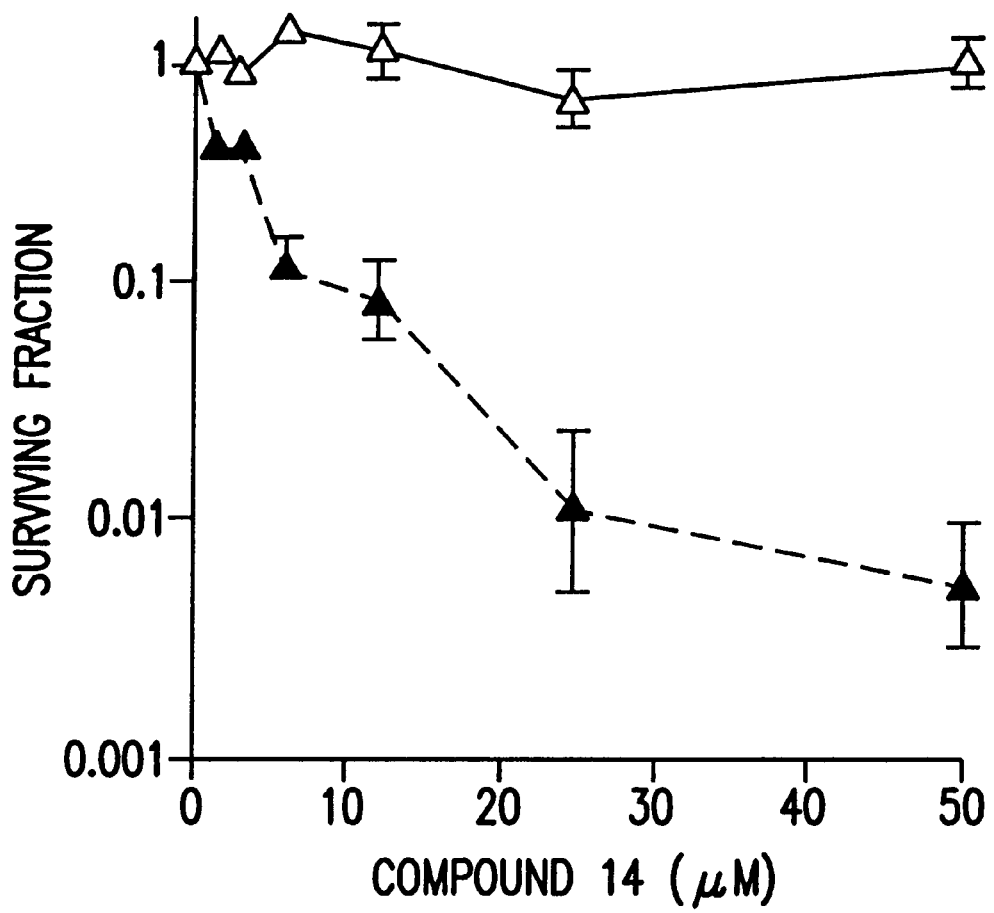
FIG. 7 is is a graph showing survival of EMT6 cells exposed to various concentrations of compound 14 for 1 hr under hypoxic or aerobic conditions in vitro.

To study the effect of replacing one of the benzylic hydrogens by a methyl group, compound 14 was evaluated for its ability to exert preferential toxicity to hypoxic EMT6 cells relative to aerobic cells (FIG. 7). Compound 14 appeared to be less toxic to aerobic EMT6 cells than compound 10h, while its hypoxic cell toxicity was essentially the same as that of compound 10h (compare FIG. 1 and FIG. 7). Points in FIG. 7 are geometric means of two or more independent determinations. Open triangles are aerobic data points and filled triangles represent hypoxic data points.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A compound of the formula

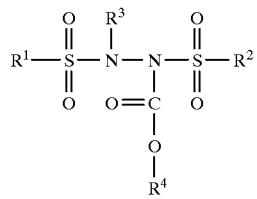

wherein
$R^1$ is selected from the group consisting of lower alkyl groups having 1–6 carbon atoms, substituted or unsubstituted aryl groups, and unsaturated alkyl groups having 2–6 carbon atoms;
$R^2$ is selected from the group consisting of lower alkyl groups having 1–6 carbon atoms, substituted or unsubstituted aryl groups, and unsaturated alkyl groups having 2–6 carbon atoms;
$R^3$ is a substituted or unsubstituted lower alkyl group having 1–6 carbons; and
$R^4$ is selected from the group consisting of substituted or unsubstituted lower alkyl groups having 1–6 carbon atoms, substituted or unsubstituted aryl groups, and unsaturated alkyl groups having 2–6 carbon atoms.

2. The compound of claim 1, wherein $R^1$ and $R^2$ are individually selected from the group consisting of methyl, ethyl, propyl, and butyl.

3. The compound of claim 1, wherein $R^3$ is selected from the group consisting of —$CH_3$ and —$CH_2$—$CH_2$—X, wherein X is a halogen atom.

4. The compound of claim 1, wherein $R^4$ is selected from the group consisting of methyl, ethyl, propyl, butyl, haloalkyl, vinyl, phenyl, p-tolyl, halophenyl, alkoxyphenyl, nitrophenyl, benzyl, nitrobenzyl, 4,5-dimethoxy-2-nitrobenzyl, halonitrobenzyl, 3-methoxy-4-nitrobenzyl, 5-methyl-2-nitrobenzyl, 1-(4-nitrophenyl)ethyl, a substituent of the formula

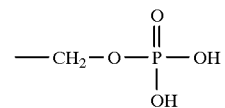

or a pharmaceutically acceptable salt thereof, and a substituent of the formula

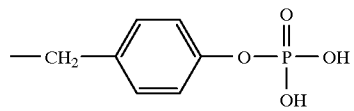

or a pharmaceutically acceptable salt thereof.

5. A pharmaceutical composition for treating tumor cells, comprising an antineoplastic agent in a pharmaceutically acceptable carrier, said antineoplastic agent having the formula

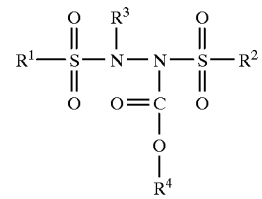

wherein
$R^1$ is selected from the group consisting of lower alkyl groups having 1–6 carbon atoms, substituted or unsubstituted aryl groups, and unsaturated alkyl groups having 2–6 carbon atoms;
$R^2$ is selected from the group consisting of lower alkyl groups having 1–6 carbon atoms, substituted or unsubstituted aryl groups, and unsaturated alkyl groups having 2–6 carbon atoms;
$R^3$ is a substituted or unsubstituted lower alkyl group having 1–6 carbons; and
$R^4$ is selected from the group consisting of a substituted or unsubstituted lower alkyl group having 1–6 carbon atoms, a substituted or unsubstituted aryl group, and an unsaturated alkyl group having 2–6 carbon atoms.

6. The pharmaceutical composition of claim 5, wherein $R^1$ and $R^2$ are individually selected from the group consisting of methyl, ethyl, propyl, and butyl.

7. The pharmaceutical composition of claim 5, wherein $R^3$ is selected from the group consisting of $CH_3$ and —$CH_2$—$CH_2$—X, wherein X is a halogen atom.

8. The pharmaceutical composition of claim 5, wherein $R^4$ is selected from the group consisting of methyl, ethyl, propyl, butyl, haloalkyl, vinyl, phenyl, p-tolyl, halophenyl, alkoxyphenyl, nitrophenyl, benzyl, nitrobenzyl, 4,5-dimethoxy-2-nitrobenzyl, halonitrobenzyl, 3-methoxy-4-nitrobenzyl, 5-methyl-2-nitrobenzyl, 1-(4-nitrophenyl)ethyl, a substituent of the formula

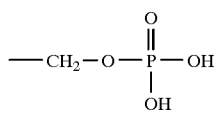

or a pharmaceutically acceptable salt thereof, and a substituent of the formula

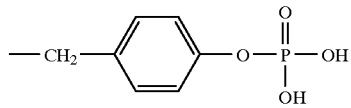

or a pharmaceutically acceptable salt thereof.

9. A method of inhibiting the growth of L1210 leukemia or EMT6 mammary carcinoma in host organisms, comprising the step of administering to said host organism a growth-inhibiting effective amount of an antineoplastic agent in a carrier, said antineoplastic agent having the formula

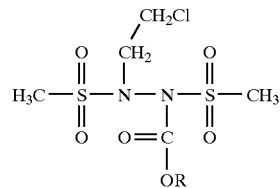

wherein R is selected from the group consisting of methyl, 2-chloroethyl, vinyl, phenyl, p-tolyl, chlorophenyl, p-methoxyphenyl, p-nitrobenzyl, benzyl, 4,5-dimethoxy-2-nitrobenzyl, 1-(4-nitrophenyl)ethyl, and a substituent of the formula

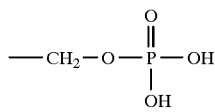

or a pharmaceutically acceptable salt thereof.

10. A compound of the formula

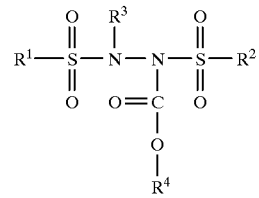

wherein $R^1$ and $R^2$ are each methyl;

$R^3$ is 2-chloroethyl; and $R^4$ is selected from the group consisting of p-nitrobenzyl, 4,5-dimethoxy-2-nitrobenzyl, 1-(4-nitrophenyl) ethyl, and combinations thereof.

11. A pharmaceutical composition for treating tumor cells, comprising an antineoplastic agent in a pharmaceutically acceptable carrier, said antineoplastic agent having the formula

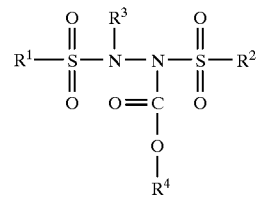

wherein $R^1$ and $R^2$ are each methyl;

$R^3$ is 2-chloroethyl; and $R^4$ is selected from the group consisting of p-nitrobenzyl, 4,5-dimethoxy-2-nitrobenzyl, 1-(4-nitrophenyl)ethyl, and combinations thereof.

* * * * *